(12) United States Patent
Crombie et al.

(10) Patent No.: US 7,300,451 B2
(45) Date of Patent: Nov. 27, 2007

(54) SUTURE ANCHORING DEVICE

(75) Inventors: John Crombie, East Hanover, NJ (US); Etan Chatlynne, Brooklyn, NY (US); John Collier, Franklin Lakes, NJ (US)

(73) Assignee: Ethicon, Inc., Somerville, NJ (US)

( * ) Notice: Subject to any disclaimer, the term of this patent is extended or adjusted under 35 U.S.C. 154(b) by 573 days.

(21) Appl. No.: 10/743,668

(22) Filed: Dec. 22, 2003

(65) Prior Publication Data

US 2005/0149121 A1  Jul. 7, 2005

(51) Int. Cl.
*A61B 17/04* (2006.01)

(52) U.S. Cl. .................. 606/232; 606/148; 128/898

(58) Field of Classification Search .............. None
See application file for complete search history.

(56) References Cited

U.S. PATENT DOCUMENTS

| | | | | |
|---|---|---|---|---|
| 374,986 | A * | 12/1887 | Meyer | 242/129.6 |
| 1,437,157 | A * | 11/1922 | Simcox et al. | 242/565 |
| 1,542,435 | A * | 6/1925 | Carlson | 242/407 |
| 1,830,014 | A | 3/1931 | Brady | |
| 2,075,508 | A | 3/1937 | Davidson | |
| 2,458,252 | A | 1/1949 | Chatterton | |
| 2,893,548 | A * | 7/1959 | Carver, Jr. et al. | 206/63.3 |
| 3,357,654 | A * | 12/1967 | Losman et al. | 242/405.3 |
| 3,361,382 | A * | 1/1968 | Converse | 242/137.1 |
| 3,409,014 | A | 11/1968 | Shannon | |
| 3,910,281 | A | 10/1975 | Kletschka et al. | |
| 4,939,820 | A | 7/1990 | Babcock | |
| 4,958,784 | A * | 9/1990 | Totten | 242/129.6 |
| 5,127,412 | A * | 7/1992 | Cosmetto et al. | 128/898 |
| 5,474,572 | A | 12/1995 | Hayhurst | |
| 5,537,776 | A | 7/1996 | Gilard | |
| 5,645,553 | A | 7/1997 | Kolesa et al. | |
| 5,893,879 | A * | 4/1999 | Hirshowitz et al. | 606/218 |
| 5,899,407 | A * | 5/1999 | Hall, III | 242/598.3 |
| 6,001,110 | A | 12/1999 | Adams | |
| 6,010,524 | A * | 1/2000 | Fleischmann | 606/213 |
| 6,066,160 | A | 5/2000 | Colvin et al. | |
| 6,106,545 | A | 8/2000 | Egan | |
| 6,120,525 | A * | 9/2000 | Westcott | 606/216 |
| 6,165,204 | A | 12/2000 | Levinson et al. | |
| 6,241,180 | B1 * | 6/2001 | Potter | 242/571.5 |
| 6,402,085 | B1 * | 6/2002 | Smith | 242/578 |
| 6,432,123 | B2 | 8/2002 | Schwartz et al. | |
| 6,902,130 | B1 * | 6/2005 | Salem | 242/395 |

FOREIGN PATENT DOCUMENTS

WO  WO 99/62406 A3  12/1999

\* cited by examiner

*Primary Examiner*—Glenn K. Dawson

(57) ABSTRACT

The present invention is directed to a suture locking device including a longitudinal retaining member having first and second ends; a support member having first and second recesses that are diametrically opposite to each other and have center points that are coaxial, where the first and second ends of the retaining member are releasably positioned within the first and second recesses of the support member. Alternatively, the suture locking device comprises a longitudinal retaining member having first and second ends; a support member having first and second recesses are diametrically opposite to each other and have center points that are coaxial, where the support member is releasably secured to hold the first and second ends of the retaining member within its first and second recesses.

15 Claims, 3 Drawing Sheets

SUTURE ANCHORING DEVICE

FIELD OF THE INVENTION

The present invention relates to a suture anchoring and tensioning device for use with sutures in surgical procedures. More particularly, the present invention pertains to an anchoring device that maintains the tension that is set by the surgeon in at least one suture in order to anchor and restrict movement of the suture at the surgical site.

BACKGROUND OF THE INVENTION

In surgical procedures, sutures are commonly used to close incisions and to reunite damaged tissue. Typically, the sutures are maneuvered and passed through the affected tissue and the free ends of the sutures are individually tied together by the surgeon. In some surgical procedures, the surgical site area is sufficiently exposed to permit the surgeon to access and tie the suture manually with a surgical knot. In other surgical procedures, such as endoscopic procedures, laparoscopic procedures, arthroscopic procedures and the like, or when robotic surgical procedures occur, the surgical site is inaccessible to the surgeon's hands. As a result, the surgeon must tie each of the suture ends into a knot at a location remote from the surgical site, and then manipulate suitably configured instruments for sliding the surgical knot to the site of the incision. Further, surgeons may tie surgical knots intracorporeally (inside of the body) using surgical tools to tie the knot down to the tissue. In general, suture knot tying is cumbersome and is one of the more time-consuming steps in the suturing process of the surgical procedure. In the foregoing circumstances, it is desirable to replace knot tying during surgical procedures in order to significantly reduce the duration of surgical operations with a device or method that is simple for the surgeon to utilize. This is especially true with regard to minimally invasive surgical procedures where the tying of surgical knots within confined spaces is extremely difficult and time consuming.

Additionally, it is noted that knots create weak points in a suture. That is to say, when a failure load is applied to a knotted suture, assuming the suture is otherwise free from imperfections, the suture will break at the knot. Therefore, elimination of surgical knots in the suture would also eliminate the weak stress points created in the suture by the surgical knot.

Suture locking and suture anchoring devices such as suture clips, surgical fasteners, hinged clips, suture terminating devices, hemostatic clips, and suture fixation devices of various configurations, designs, structures, and materials of construction are well known in the prior art. For example, U.S. Pat. No. 2,075,508 discloses a suture retainer whereby a suture may be fixed relative to a surgical button. The suture is received and wedged between the button and a clamping plate in order to securely clamp the suture. There are a number of shortcomings to this retainer. First, due to the suture manipulation required to use this retainer, a laparoscopic applicator device would be extremely difficult to produce profitably. Furthermore, the wedging and clamping action will induce stress concentrations in the suture, which likely lead to reduced failure loads.

U.S. Pat. No. 6,432,123 to Schwartz et al. discloses a device comprised of a locking ring formed to have an aperture that allows a suture to pass when the suture is pulled in a first direction, but formed to lock the suture in place when the suture is pulled in an opposite direction. A locking ring is employed to compress the device upon the suture, thereby causing an increased stress concentration in the suture and thereby diminishing the failure load of the suture. Furthermore, as depicted, this device requires the user to thread the suture through a small aperture following wound approximation.

U.S. Pat. No. 6,066,160 to Colvin, et al. discloses a suture terminator device for use in minimally invasive surgery. The suture terminator device includes a pair of locking aperture with teeth for engaging a portion of a suture at the locking aperture's threaded end. Not only does this device require laparoscopically guiding two strands of suture between two very small apertures, it also requires that the sutures be squeezed tightly by these teethed apertures, thereby diminishing the integrity of the suture and significantly reducing the maximum tension the suture can withstand.

U.S. Pat. No. 6,106,545 to Egan discloses a suture tensioning and fixation device, which includes a retaining element for frictionally engaging a suture that may subsequently be melted to bond to the suture for a permanent fixation. This melting and bonding action will compromise the integrity of the suture and therefore, because suture strength is of utmost concern in most surgeries, this method of fixation of the retaining element to the suture is not suitable for most surgeries.

U.S. Pat. Nos. 5,474,572 to Hayhurst and 5,645,553 to Kolesa et al. disclose the use of a hinged clip that snaps closed after the suture threads are placed within the holding members. The hinge clip is snapped into place such that the suture is held transversely across the holding members, thus locking the suture in place. There is a possibility of improperly actuating or inadvertently releasing the snap, which could lead to an insecure fixation of the suture. In addition, weak stress points are created where the suture is held within the clip.

In view of the deficiencies of the prior art discussed hereinabove, there remains a need for a suture anchoring device that is simple to use, particularly during laparoscopic surgery, in order to eliminate manual knot tying by the surgeon performing the surgical procedure, while not compromising the integrity of the suture.

SUMMARY OF THE INVENTION

One embodiment of the present invention is directed to a suture locking device comprising a longitudinal retaining member having first and second ends; a support member having first and second recesses that are diametrically opposite to each other and have center points that are coaxial, where the first and second ends of the retaining member are releasably positioned within the first and second recesses of the support member.

Alternatively, the suture locking device comprises a longitudinal retaining member having first and second ends; a support member having first and second recesses that are diametrically opposite to each other and have center points that are coaxial, where the support member is releasably secured to hold the first and second ends of the retaining member within its first and second recesses.

A method of closing an incision is also disclosed, where the method comprises the steps of suturing the incision with a suture to form a closed incision; introducing the portion of the suture that remains at the final suture exit from the tissue surface to a longitudinal retaining member having first and second ends; wrapping the suture around the retaining member by rotating the retaining member in the direction of the closed incision; guiding the retaining member along the path formed by the suture to the closed incision; positioning the first and second ends of the retaining member in first and second recesses of a support member, where the first and second recesses are diametrically opposite to each other and have center points that are coaxial, to form a suture locking device where the innermost portions of the surfaces of the suture locking device, relative to the center of gravity of the device, bound the sides of a volume having a cross sectional area that is parallel to the longitudinal axis of the retaining member wherein the projection of said cross section upon the tissue surface defines a free area, such that the final suture exit is bounded by this free area.

DETAILED DESCRIPTION OF THE INVENTION

The present invention provides a suture anchoring device that is comprised in part of a longitudinal retaining member having first and second ends. Optionally, the retaining member may be made from one or more sections. The invention is further comprised in part of a support member having first and second recesses that lie diametrically opposite to each other and having center points that are coaxial. In use, the first and second ends of the retaining member are releasably positioned within the first and second recesses of the support member. Alternatively, the support member is releasably secured to hold the first and second ends of the retaining member. When used in a surgical procedure, a suture is enwrapped tightly around the retaining member, the retaining member is positioned atop the wound site and the retaining member is releasably positioned within the first and second recesses of the support member or the support member is releasably secured to hold the first and second ends of the retaining member, thereby maintaining the position and orientation of the retaining member and the suture. The suture anchoring device described herein advantageously anchors and tensions the suture without inducing stress concentrations in the suture that may lead to reduced failure loads.

The suture anchoring device described herein can be used in combination with multiple sutures or with a single suture for various types of surgical procedures by surgeons. The suture anchoring device may be fabricated from any biocompatible medical material, such as polymeric or metallic. The polymeric material may be absorbable within a mammalian body (e.g. polydioxanone such as poly(1,4-dioxan-2-one), polymers or copolymers of organic hydroxyesters, polyglycolide, polylactide, polyhydroxy butyric acid, polycaprolactone, polytrimethylene carbonate and polyvinyl alcohol), or it may be non-absorbable (e.g. polyolefins such as polyethylene or polypropylene, polyesters, fluorpolymers such as polytetrafluoroethylene, polyamides such as nylon, and combinations thereof). Furthermore, the suture anchoring device may be fabricated via standard machining processes, injection molding, or a lithographic process (e.g. stereolithography).

Figure 1:
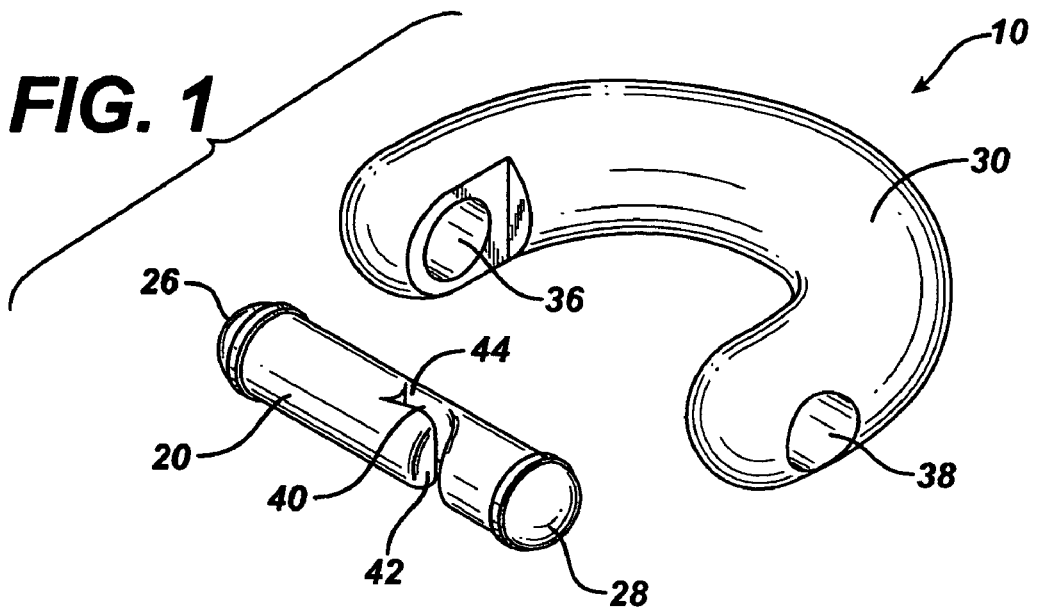
FIG. 1 is a perspective view of a suture anchoring device constructed in accordance with one embodiment of the present invention, the device being shown in a disassembled state.
Figure 2:
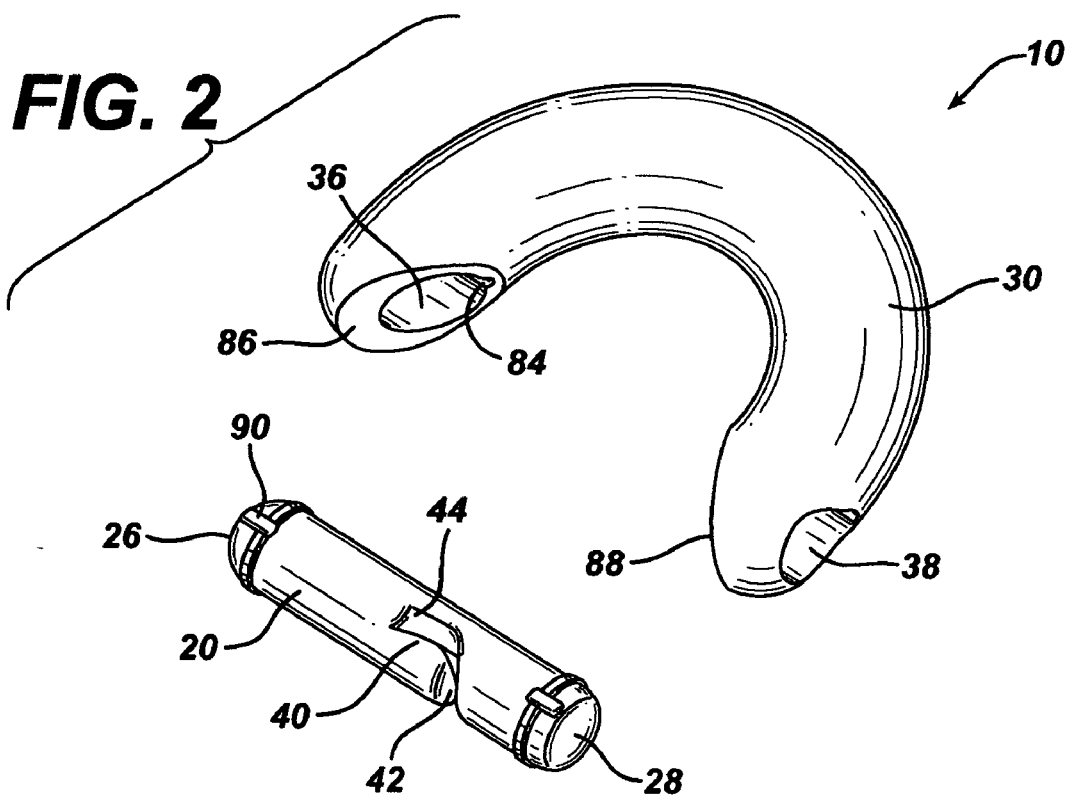
FIG. 2 is similar to FIG. 1 except that the suture anchoring device has two angled surfaces.

Referring to FIG. 1, there is shown a suture anchoring device 10 for use in surgical procedures for anchoring and tensioning sutures. The suture anchoring device may be comprised in part of a longitudinal retaining member 20 having a first end 26, and a second end 28. Suture anchoring device 10 is further comprised of a support member 30 having a first recess 36, and a second recess 38 that are diametrically opposite to each other and have center points that are coaxial. So comprised, first end 26 and second end 28 of retaining member 20 may be releasably positioned within first recess 36 and second recess 38 of support member 30 or support member 30 may be releasably secured to hold the first and second ends 26 and 28 of retaining member 20. Because the fabrication materials described may be somewhat resilient, support member 30 may flex to accept retaining member 20 such that first end 26 and second end 28 of retaining member 20 may be releasably positioned within first recess 36 and second recess 38 of support member 30. Referring to FIG. 2, in another embodiment, the surfaces 86 and 88 of support member 30 adjacent to recesses 36 and 38 may be angled to facilitate insertion of first end 26 and second end 28 of retaining member 20.

Support member 30 may have a geometric shape. Alternatively, support member 30 may have an arcuate or rectangular shape and a geometric cross section. The support member 30 may be made from one or more sections. For example, the support member may be formed of two sections, each section having one of the recesses, where the two sections are releasably interlocking such that the support member securely holds the longitudinal retaining member when the two sections of the support member are interlocked over the ends of the retaining member Recesses 36 and 38 of support member 30 may be geometrically shaped. In another embodiment recesses 36 and 38 are non-circularly shaped to prevent rotation of first end 26 and second end 28 of retaining member 20. In another embodiment recesses 36 and 38 are asymmetrically shaped to prevent rotation of first end 26 and second end 28 of retaining member 20. In another embodiment recesses 36 and 38 have a key recess 84, as shown in FIG. 2, to prevent rotation of first end 26 and second end 28 of retaining member 20.

Retaining member 20 may have a geometric cross section. Optionally, retaining member may be made from one or more sections. For example, the retaining member may be a first member having a first diameter that fits over a second member having a smaller diameter, with a spring that fits inside the smaller diameter second boss member and extends into the larger diameter first boss member. In another embodiment first end 26 and second end 28 of retaining member 20 are non-circularly shaped to prevent rotation within support member 30, which may optionally have recesses 36 and 38 of a similar shape to first end 26 and second end 28 of retaining member 20. Alternatively, first end 26 and second end 28 of retaining member 20 are asymmetrically shaped to prevent rotation within support member 30. In another embodiment first end 26 and second end 28 of retaining member 20 have at least one key feature 90 to prevent rotation within support member 30.

Figure 3:
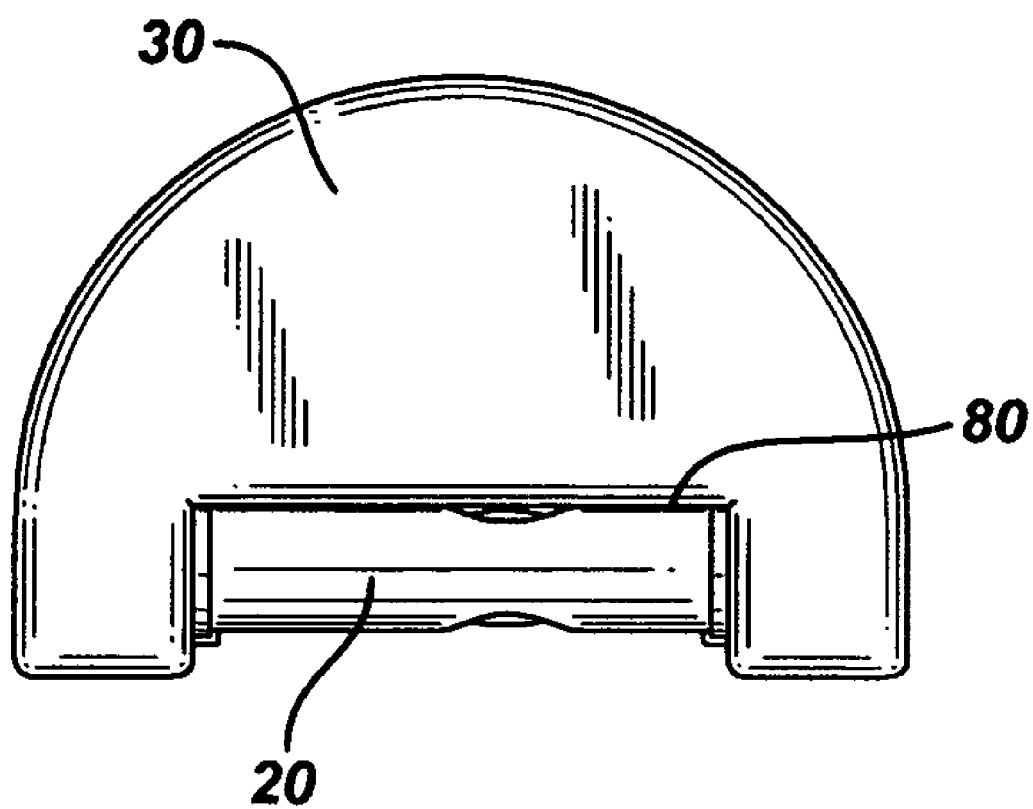
FIG. 3 is a top view of a suture anchoring device where the free area between the retaining member and the support member is on the order of the diameter of a suture.
Figure 4A:
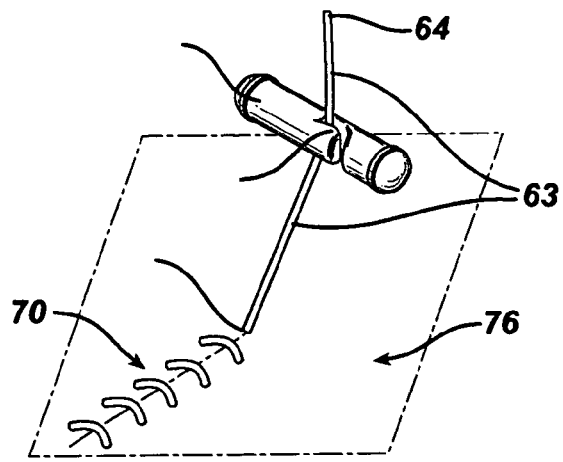
FIGS. 4a to 4d are schematic representations that illustrate the steps involved in the attachment of a suture to the suture anchoring device of FIG. 1.
Figure 4B:
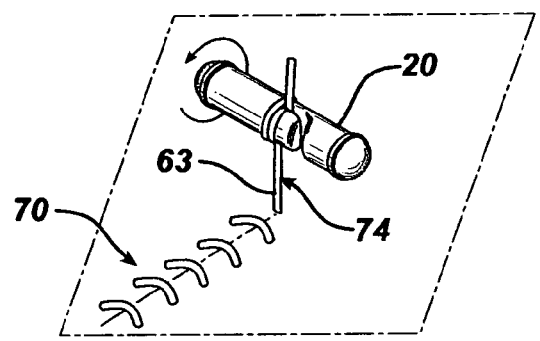
Figure 4C:
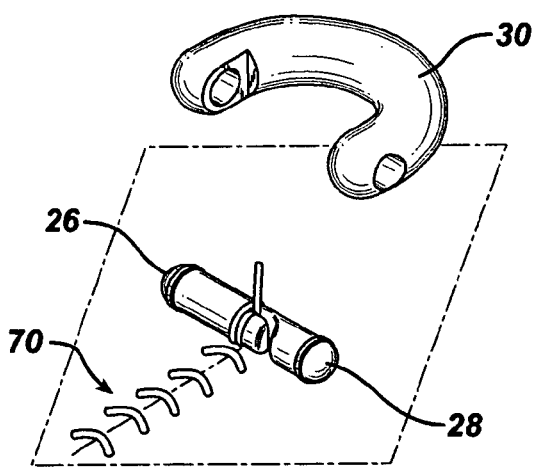
Figure 4D:
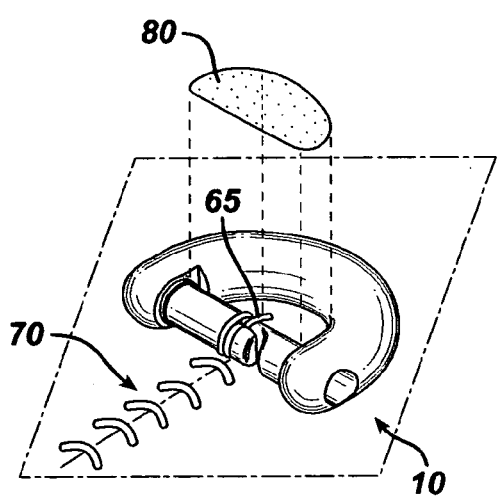

Referring to FIGS. 3 and 4d, when retaining member 20 is positioned within support member 30, the innermost portions of the surfaces of device 10, relative to the center of gravity of device 10, bound the sides of a volume having a cross sectional area that is parallel to the longitudinal axis of retaining member 20. The projection of said cross section upon the tissue surface defines free area 80. Referring to FIG. 3, free area 80 is a gap formed between the adjoining edges of the support member and the retaining member wherein the width of the gap is on the order of the diameter of a suture.

Optionally, retaining member 20 may have an opening 40 that extends from the surface 42 of retaining member 20 to an inner point 44 of retaining member 20. The width of opening 40 may be sized to permit the entrance of one or more sutures.

The suture anchoring device can be used in combination with multiple sutures or with a single suture in various surgical procedures by surgeons to fixate sutures in the surgery. Reference made herein to a suture may include one or more sutures. Furthermore, reference made herein to a suture pertains specifically to the portion of the suture 63 between the suture free end 64 and the suture exit 65 from a closed incision 70 on a tissue surface 76, as illustrated in FIG. 4. The standard suturing procedure for tissue approximation, prosthetic fixation or the like, is performed until the step of the procedure at which knot tying would typically commence. At this point, the knot tying steps are replaced with the steps for employing the suture anchoring device 10. For example, retaining member 20 is brought into contact with suture 63 in the proximity of free end 64, wherein the user either places suture 63 into opening 40, as shown in FIG. 4a, or manually wraps suture 63 at least once around retaining member 20. Second, suture 63 is pulled taut and is wrapped around retaining member 20 by rotating retaining member 20 in the direction of the closed incision 70 while maintaining suture 63 in a taut state. This wrapping action may be performed manually by the surgeon or with the aid of a separate device designed to aid in the deployment of suture anchoring device 10. Retaining member 20 is guided to closed incision 70 along the path 74 formed by suture 63, as shown in FIG. 4b. Once at closed incision 70, as seen in FIG. 4c, first end 26 and second end 28 are positioned in first recess 36 and second recess 38 of support member 30 to form the suture anchoring device 10. Retaining member 20 and support member 30 define a free area 80, such that suture exit 65 is adjacent to or bounded by the free area 80, as shown in FIG. 4d. Following deployment, the suture is anchored securely to suture anchoring device due to the static equilibrium of the system wherein the system is comprised of the suture anchoring device, the suture and the tissue. That is to say, the net force and net moment on the suture and the suture anchoring device are zero because the suture anchoring device and the tissue are in a compressive state while the net moment imparted to the retaining member by the suture is counteracted by the reactive moment of the tissue upon the support member such that the support member maintains the position of the retaining member. In utilizing the suture anchoring device of the present invention, the surgeon is able to set a tension on the suture that may be maintained without the use of surgical knots and without the creation of stress concentrations in the suture, such that the suture movement is restricted at the surgical site As discussed above, the suture anchoring device may be used manually, i.e., applied by the surgeon using hands, or with any surgical instruments (e.g. laparoscopic instruments) suitable for suture manipulation, tissue manipulation, or the like. Furthermore, a laparoscopic device that is specifically designed to automate the anchoring method may be used.

It should be understood that the invention and embodiments described herein serve to merely illustrate the preferred concepts and that a person skilled in the art may make many variations and modifications without departing from the spirit and scope of the present invention. All such variations and modifications are intended to be included within the scope of the invention as defined in the claims.

What is claimed:

1. A method of closing an incision, comprising the steps of:
   a) suturing the incision with a suture to form a closed incision;
   b) introducing the portion of the suture that remains at the final suture exit from the tissue surface, to a longitudinal retaining member having first and second ends;
   c) wrapping the suture around the retaining member by rotating the retaining member in the direction of the closed incision;
   d) guiding the retaining member along the path formed by the suture to the closed incision; and
   e) positioning the first and second ends of the retaining member in first and second recesses of a support member, where the first and second recesses are diametrically opposite to each other and have center points that are coaxial, to form a suture locking device where the retaining member and support member define a free area, such that the final suture exit is bounded by or is adjacent to the free area.

2. The method of claim 1 where the support member has a geometric or arcuate shape.

3. The method of claim 1 where the support member has an arcuate shape and a geometric cross section.

4. The method of claim 1 where the support member has a rectangular shape and a geometric cross section.

5. The method of claim 1 where the retaining member has a geometric cross section.

6. The method of claim 1 where the retaining member has an opening that extends from the surface of the retaining member to an inner point on the retaining member.

7. The method of claim 6 where the width of the opening is sized to permit entrance of at least one surgical suture.

8. The method of claim 1 where the recesses on the support member are geometrically shaped.

9. The method of claim 1 where the recesses on the support member are non-circular.

10. The method of claim 1 where the recesses on the support member are asymmetric.

11. The method of claim 1 where the recesses on the support member are keyed.

12. The method of claim 1 where the first and second ends of the retaining member are non-circular.

13. The method of claim 1 where the first and second ends of the retaining member have asymmetric cross sections.

14. The method of claim 1 where the first and second ends of the retaining member are keyed.

15. The method of claim 1 where the support member has at least two angled surfaces.

* * * * *